United States Patent [19]
Eisenberg

[11] Patent Number: 6,039,760
[45] Date of Patent: *Mar. 21, 2000

[54] COMPOSITE LIVING SKIN EQUIVALENT

[75] Inventor: Mark Eisenberg, Dover Heights, Australia

[73] Assignee: Ortec International, Inc., New York, N.Y.

[ * ] Notice: This patent is subject to a terminal disclaimer.

[21] Appl. No.: 08/602,271

[22] Filed: Feb. 16, 1996

Related U.S. Application Data

[60] Continuation of application No. 08/123,860, Sep. 20, 1993, abandoned, which is a division of application No. 07/777,419, Nov. 27, 1991, Pat. No. 5,282,859.

[30] Foreign Application Priority Data

Apr. 24, 1990 [AU] Australia .................................. PJ9819
Jan. 22, 1991 [AU] Australia .................................. PK4302

[51] Int. Cl.$^7$ ...................................................... A61F 2/10
[52] U.S. Cl. .............................. 623/15; 435/240; 424/424
[58] Field of Search ................................... 623/11, 12, 1, 623/2, 15, 16, 66; 424/424; 435/240

[56] References Cited

U.S. PATENT DOCUMENTS

| | | | |
|---|---|---|---|
| 4,673,649 | 6/1987 | Boyce, et al. ............................ | 435/240 |
| 4,703,108 | 10/1987 | Silver et al. ............................ | 540/356 |
| 4,940,666 | 7/1990 | Boyce et al. ........................ | 435/240.2 |
| 5,282,859 | 2/1994 | Eisenberg .................................. | 623/15 |

FOREIGN PATENT DOCUMENTS

| | | | |
|---|---|---|---|
| 8808305 | 11/1988 | WIPO ...................................... | 623/66 |
| WO88/08305 | 11/1988 | WIPO ...................................... | 623/15 |

OTHER PUBLICATIONS

Boyce, et al, Biologic Attachment, Growth, and Differentiation of Cultured Human Epidermal Keratinocytes on a Graftable Collagen and Chondroitin–6–Sulfate Substrate, Surgery, Apr. 1988, pp. 421–430.

Boyce, et al. Biological Attachment, Growth & Differentiation of Cultured Human Epidermal Keratinocytes on Graftable Collagen and Chondroitin–6–Sulfate Substrate; Surgery Apr. 1988, pp. 421–431.

Primary Examiner—David J. Isabella
Attorney, Agent, or Firm—Ralph T. Lilore

[57] ABSTRACT

Skin equivalents and processes for preparing them are described. The living skin equivalent comprises a layer of cultured keratinocyte cells, a layer of high purity, non-porous collagen and a dermal layer of cultured fibroblast cells in a porous, cross-linked collagen sponge. Processes are described for producing the skin equivalent with descriptions on how to obtain and treat skin precursor materials to yield suitable fibroblasts and keratinocytes.

The collagen layers, the physical forms thereof, and treatments thereof are also described. Preferably, the non-porous, highly-purified collagen is selected from Type 1, Type 3, or mixtures of Type 1 and Type 3 collagen. The collagen is purified ideally by treatment with pepsin, to remove antigenic substances.

The collagen sponge used can be any suitable form of collagen sponge which will support fibroblast growth.

The keratinocytes used in the invention are preferably prepared by the "drop" method spotted evenly on culture media and incubated to coalescence.

13 Claims, 5 Drawing Sheets

FIG. 2b (NORMAL SKIN)

COMPOSITE LIVING SKIN EQUIVALENT

This application is a continuation of application No. 08/123,860, filed Sept. 20, 1993, now abandoned which is a division of application Ser. No. 07/777,419, filed Nov. 27, 1991 now U.S. Pat. No. 5,282,859.

TECHNICAL FIELD

The present invention relates to living skin equivalents and, in particular, to composite living skin equivalents comprising an epidermal layer of cultured keratinocyte cells, a layer of highly purified, non-porous collagen and a dermal layer of cultured fibroblast cells in a porous, cross-linked collagen sponge. The invention also relates to a method of preparing the composite living skin equivalent.

BACKGROUND ART

Skin equivalents have many uses not only as a replacement for human or animal skin for skin grafting, but also as test skin for determining the effects of pharmaceutical substances and cosmetics on skin.

A major difficulty in pharmacological, chemical and cosmetic testing is the difficulties in determining the efficacy and safety of the products on skin. One advantage of the skin equivalents of the invention is their use as an indicator of the effects produced by such substances through in vitro testing on test skin.

Also, skin grafting of denuded areas, of granulating wounds and of burns, still present major healing problems despite advances in grafting techniques. Split thickness autografts and epidermal autografts (cultured autogenic keratinocytes) have been used with variable success. However, both forms of treatment have many disadvantages. For example, split-thickness autografts are generally unavailable in large body surface area (BSA) burns, cause further injury to the patient, are of limited use in the treatment of patients with Dystrophic Epidermolysis bullosa (DEB), show limited tissue expansion, require repeated surgical operations and protracted hospitalization and give rise to undesirable cosmetic results. Epidermal autografts require time to be produced, have a low success ("take") rate of between 30–50%, often form spontaneous blisters, are fragile and difficult to handle, exhibit contraction to 60–70% of their original size, are vulnerable during approximately the first 15 days after grafting and are of virtually no use in the treatment of deep burns where both the dermis and epidermis have been destroyed.

An alternative form of treatment is epidermal allografts (cultured allogenic keratinocytes). American researchers have treated patients with second degree burns by grafting epidermal allografts onto wounds with some success. The benefits of such an allograft include: a ready supply of such grafts can be maintained so that the patients might be covered in a single procedure with a material which allows permanent healing to occur, it eliminates autografting which increases the area of wounds and leaves painful infection-prone donor sites, burn wounds covered with cultured allografts heal as quickly as burn wounds that have been covered with autografts, and enables the treatment of patients with DEB.

However, epidermal allografts still experience many of the limitations of epidermal autografts.

Full thickness skin injuries from burns destroy both the epidermis and dermis, and treatment With cultured skin needs to replace both of these components.

Hansborough, J. F and Boyce, S. T (JAMA 1989, 2125–2130) reported the application of auto epidermal cells onto a dermal equivalent which is then grafted onto a wound. The main disadvantage of this method lies in the preparation of the dermal equivalent.

Furthermore, this method involved the use of chondroitin-6-sulfate (GAG) which has weak bonding to the collagen at neutral pH, and thus may be released into the wound environment causing unforeseen long term effects on human subjects. GAG has been reported to increase scar formation in wounds which is something to be avoided in grafts. Another effect of GAG containing collagen sponges consisting in reduction of collagen blood clotting capacity can be considered rather unfavourable for application in bleeding wounds. Fibrin clot contributes to an adhesion of the graft to the wound.

Also, in this method, the collagen sponge is stabilized by being crosslinked with with 0.25% glutaraldehyde (GTA). Such crosslinked collagen is resorbed at a slower rate and is resistant to bacterial or fungal infection. At the same time the ingrowth of cells, infiltrating the GTA crosslinked collagen matrix-is less. Collagen crosslinked with GTA may retain this agent as a high molecular weight polymer which is continuously hydrolyzed and monomeric GTA is released and detactable for up to 6 weeks. The cytotoxic effect of GTA on fibroblasts in tissue culture suggests that it is not an ideal crosslinking agent for a dermal equivalent which is infiltrated by hosts cells and in which the bovine collagen matrix is rapidly degraded thus releasing GTA into body fluids.

Recently, living skin equivalent grafts comprising a dermal layer of rat fibroblast cells cast in soluble collagen and a epidermal layer of cultured rat keratinocytes were successfully grafted as allografts onto Sprague Dawley rats by Bell et.al. (Journal Investigative Dermatology,1983; 81:2s-10s). Histological examination of the graft revealed that the epidermal layer had fully differentiated to form desmosomes, tonofilaments, keratohyalin and a basement lamella. However, attempts to reproduce the living skin equivalent using human fibroblasts and keratinocytes met only with limited success. The keratinocytes failed to fully differentiate to form a basement lamella and the dermo-epidermal function was a straight line.

Problems of epidermalizing the surface of the above dermal equivalent resulted in Bell modifying his method by using skin biopsies as a source of keratinocytes, as described in the International PCT application, published as WO 86/02273. The problems with this approach are that the skin substitute thus produced is not uniform over its entire surface, since the biopsy, including the dermal portion, remains inserted in the dermis substitute. Also, the surface-area of the skin substitute obtained is limited by the number of biopsies that may be taken from a single person. The biopsy taking involve a medical procedure with potential problem of infection and scar formation. The punch biopsies of skin equivalent as a means of expanding the production of additional skin equivalent is a time consuming process. As a result, such a skin equivalent has not been used clinically. In 1988, a paper in the journal "Burns" by Colounb et al reported a 100% failure rate using Bell's method.

Bernard et al, the inventors of Australian Patent Application AU-A-13743/88 try to avoid the above problems by utilizing the culturing capacity of keratinocytes contained in the sheath of a hair follicle. The skin biopsy is replaced by a hair follicle enclosed in its sheath, which is implanted in a perpendicular position in the free surface of dermis substitute being formed. The main criticism of the above invention is the nature of the dermis and the fact that the period of epidermal growth may take several months.

Thus, there is a need for the development of living skin equivalent grafts comprising both the epidermal and dermal layers that can be easily prepared and maintained in sufficient quantities to enable a single treatment of skin wounds.

In developing a living skin equivalent it is desirable that it comprise at least some or all of the following features: it should enable rapid and sustained adherance to the wound surface, it should be tissue comparable, it should have an inner surface in contact with the wound surface that promotes the ingrowth of fibrovascular tissue, and/or it should provide protection from infection and prevention of fluid loss.

It is therefore an object of the present invention to provide cultured living skin equivalents that exhibit at least some of these features and which will substantially overcome, or ameliorate one or more of the abovementioned problems.

DISCLOSURE OF THE INVENTION

One aspect of the present invention concerns composite living skin equivalents comprising an epidermal layer of cultured keratinocyte cells, a layer of high purity, non-porous collagen and a dermal layer of cultured fibroblast cells in a porous, cross-linked collagen sponge.

Another aspect of the present invention involves a process for the preparation of composite living skin equivalents which comprises: obtaining a skin sample, treating the skin sample enzymically to separate the epidermis from the dermis, treating the epidermis enzymically to release the keratinocyte cells, culturing the epidermal keratinocytes until confluence, in parallel, or separately, treating the dermis enzymatically to release the fibroblast cells, culturing the fibroblasts cells until sub-confluence, inoculating a porous, cross-linked collagen sponge membrane with the cultured fibroblast cells, incubating the inoculated collagen sponge on its surface to allow the growth of the fibroblast cells throughout the collagen sponge, inverting the collagen sponge, and laminating the other surface of the sponge with a thin layer of high purity, preferably pepsin treated, non-porous collagen to form a layered sponge complex, incubating the complex to polymerize the non-porous collagen, and then inoculating it with cultured keratinocyte cells, and incubating the composite skin equivalent complex to promote the growth of the cells.

Preferably the primary culture of fibroblasts is prepared by: obtaining a dermal sample, suspending the dermal sample in a solution of collagenase to release the fibroblast cells, incubating the culture, centrifuging the culture to produce a cell pellet of fibroblasts, removing the culture medium, washing the cell pellet to remove extraneous culture medium, determining the cell number and viability, inoculating culture flasks with the cells and culturing to subconfluence.

Preferably the non-porous, highly purified collagen is selected from Type 1, type 3, or mixtures of type 1 and type 3 collagen. For example, a suitable bovine hide collagen is that obtainable from Sigma.

The collagen is purified ideally by treatment with pepsin, to remove antigenic substances.

The collagen sponge used can be any suitable such collagen sponge, for example that obtainable from Mitaplast.

The keratinocytes used in the invention are preferably prepared by the "drop" method. The keratinocytes are released from the epidermis to provide a single cell suspension. Separate drops of this suspension are spotted evenly on culture media and incubated, so that the cells spread and eventually coalesce.

BRIEF DESCRIPTION OF THE DRAWINGS

The invention will now be described by way of non-limiting examples and with reference to the accompanying illustrations wherein.

MODES FOR CARRYING OUT THE INVENTION

Figure 1:
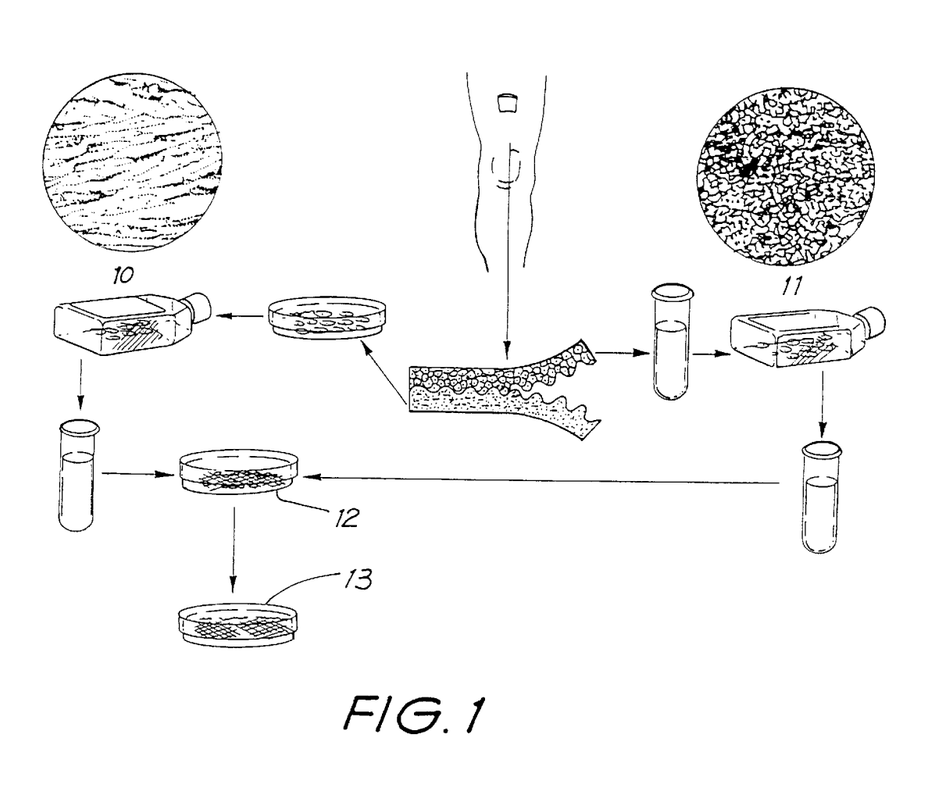
FIG. 1 is a schematic representation of the process for producing the composite living skin equivalents of the present invention.
Figure 2A:
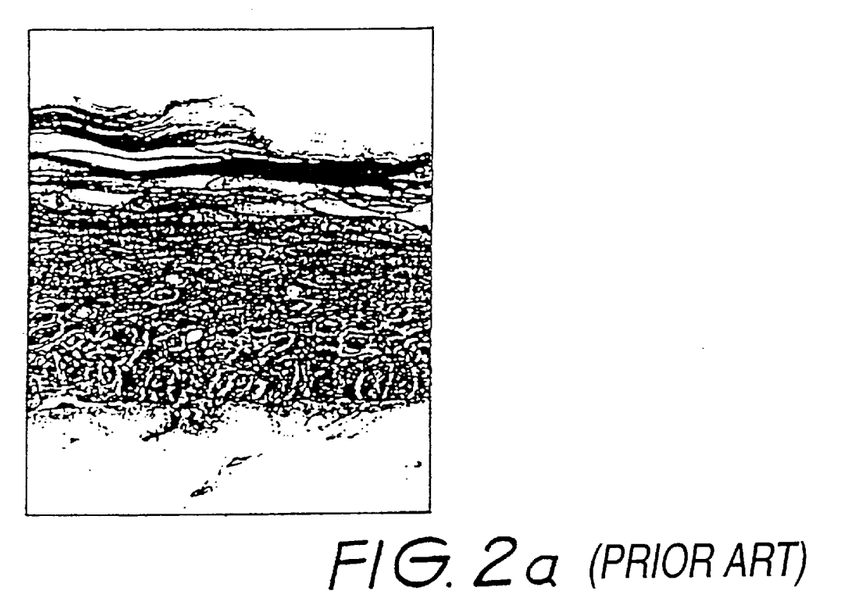
FIG. 2a) shows the histological appearance of the composite living skin equivalent shown in the 1987 Annual Report of the Organogensis Company, 150 Dan Road, Canton, Mass. 02021, compared to Figure b) which shows the histological appearance of normal skin as shown in that same Report.
Figure 2B:
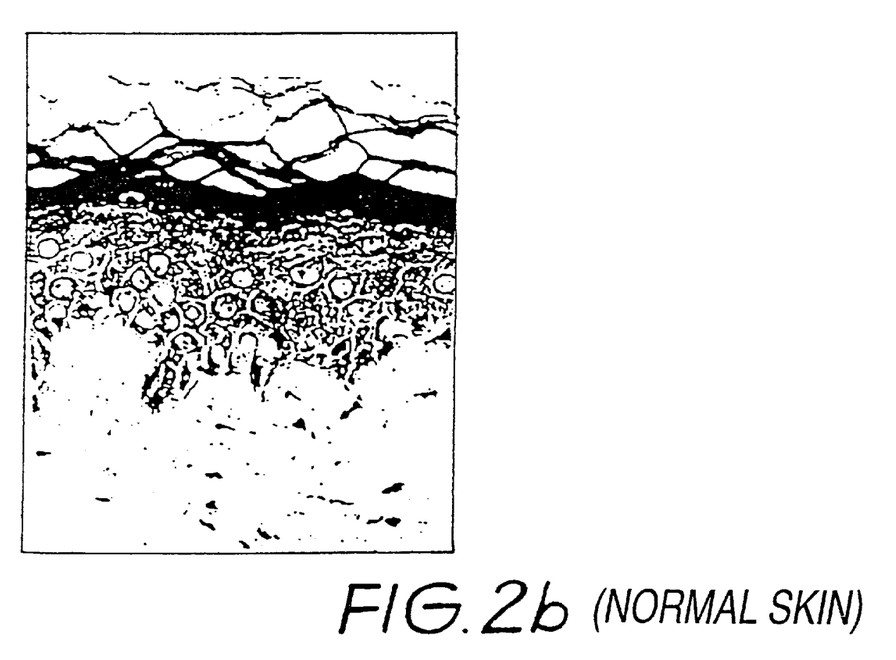

FIG. 1 shows schematically the process for the preparation of the composite living skin equivalent.

In FIG. 1, a skin sample is separated into dermis being used as a source of fibroblasts (10), and the epidermis being used as a source of keratinocytes (11). The cultured fibroblasts (10) are inoculated into the collagen sponge (12), and after the fibroblasts colonise the sponge, the other side off the sponge is inoculated with the pepsin treated non-porous collagen. After further incubation, the non-porous collagen is inoculated with the keratinocyte culture, preferably by the "drop" method, and cultured, to eventually produce the skin equivalent (13).

Any skin sample amenable to cell culture techniques can be used in accordance with the present invention. The skin samples may be autogenic or allogenic.

Skin samples are treated with trypsin to separate the epidermis from the dermis (Eisinger, M. Method in Skin Research, Editor D. Skerrow, (1985) pp 193). The epidermis is minced and treated with trypsin to release the keratinocyte cells. The keratinocyte cells are cultured until confluence using standard methods. In a preferred aspect, the keratinocyte cells are cultured as single cell suspensions until confluence.

Primary cultures of fibroblast cells for use in accordance with the present invention may be prepared using standard methods such as, for example, the method disclosed in "A specific collagenase from Rabbit fibroblasts in monolayer culture" (Journal of Biochemistry (1974) 137, 373–385). Preferably, the primary cultures of fibroblast cells are prepared by the following method.

A dermal sample is cut up into 1 mm cubes and is suspended in a solution of collagenase buffered with Tris-HC1 pH 7.4. Dermal samples may be allogenic or autogenic. A suitable collagenase is *Clostridium histolyticum* collagenase. The dermal sample is preferably suspended in solution at a concentration of 1 microgram/ml. The suspension is incubated and then centrifuged at 1,500 rev/sec to remove the cells from solution. The suspension is preferably incubated for 30 minutes. The cell pellet is washed with DMEM and the number of fibroblasts cells is determined with a haemocytometer. The viability of the fibroblast cells is determined by dye exclusion using Trypan Blue. The fibroblast cells may be injected directly into collagen sponges or are used to seed culture flasks and grown to sub-confluence using standard methods. Surprisingly, this method is shorter by up to 2 weeks than other known methods which take up to 3 weeks to prepare primary cultures of fibroblasts.

The above culturing method also surprisingly yields other dermal epithelical cells which have a potential to develop into sweat glands or other skin cell types.

Cross-linked, bovine collagen sponge membranes are obtained commercially and are stored frozen. Before use, the sponges are washed with sterile water and dehydrated at 37° C. to compact the membranes.

The collagen sponge is inoculated with cultured fibroblast cells. In one embodiment, the sponge is inoculated with subconfluent cell culture. Preferably, the fibroblast inoculum has a density of about $4 \times 10^5$ cells/ml.

The inoculated sponge is incubated using standard methods to enable the growth of the fibroblast cells throughout the collagen matrix. In one embodiment, the sponge is incubated at 37° C., with 5% $CO_2$ and saturated humidity for 10 days in DMEM and conditioned media. The DMEM and conditioned media is preferably changed every second day. Conditioned media is DMEM which has been used in the culture of human keratinocytes over a period of 2 days. It contains various macromolecules secreted by the keratinocytes which are known to stimulate fibroblasts. The conditioned media can be stored frozen until use. It is used in conjunction with fresh DMEM in a ratio of 1:2.

The sponge is then inverted and the upper surface is laminated with pepsin-treated, non-porous collagen. In one embodiment of the present invention, the laminate layer is (purified) pepsin-treated, non-porous, sterile type 1 bovine collagen, or a mixture of type 1 and 3 bovine collagen. The bovine collagen is obtained commercially in substantially purified form. It is treated with pepsin using the method of Drake, M. P., Davison, P. F. and Bump, S. (1966) Biochemistry 5:301–312, to remove teliopeptides. The pH of the collagen solution is adjusted to neutral pH and is sterilized with Gamma radiation. A suitable concentration of the collagen solution is 2 mg/ml. The collagen is layered as a thin film onto the sponge and is incubated to complete polymerization of the collagen at 37° C. for 60 minutes.

Cultured keratinocytes are then inoculated onto the laminate layer. Preferably, the cells are inoculated with drops of media containing cells at a density of $1 \times 10^5$ cells/drop. The sponge is then incubated in DMEM supplemented with 2% fetal bovine serum, 10 ng/ml human epidermal growth factor, 0.4 mg/ml hydrocortisone and $10^{-9}$M cholera toxin at pH 7.2 and 35° C. for 10 days.

The skin equivalent remains immersed in the above culture medium throughout the incubation period.

Prior to the clinical or in vitro application of the composite living skin equivalent, medium without bovine pituitary extract is added to the culture medium.

Surprisingly, in clinical applications, the composite living skin equivalent of the present invention results in a rapid normalization of the interface between the epidermis and dermis of the healed transplants. Histological examination of the skin equivalent of the present invention after 2 weeks culture in vitro revealed a multilayered epidermis growing on a homogeneous membrane. Histological examination of a biopsy sample of a skin equivalent of the present invention taken 2 weeks after grafting confirmed the formation of stratun corneum with a fully keratinized epidermis on a dermis populated by non-inflammatory connective tissue cells Significantly there is an undulating and morphologically mature epidermal-dermal junction when viewed by light and electron-microscopy. There was an interdigitations of rete ridges and dermal papillae that are characteristic of normal skin and are important if the interface between the epidermis and the dermis are to be normalized.

If the skin equivalent is cultured initially immersed for 4 days in the DMEM culture medium with a $Ca^{++}$ of $0.05 \times 10^{-3}$M and then for 10 days with the epidermis exposed (air liquid interphase) in DMEM medium containing a raised concentration of $Ca^{++}$ of $0.05 \times 10^{-3}$M then its possible to detect a multilayered, differentiated epidermis which consists of a basal cell layer on a well developed basal lamina and several layers of suprabasal cells which show early keratinization.

The above in vitro system closely resembles human skin instructural arrangement and biosynthetic output and may be adapted to test the safety of chemicals pesticides and skin irritation of cosmetic substances. Test substances applied to the surface of this system may cause irritation of the cells and trigger the release of mediators of the inflammatory response which can be measured in the culture fluid. This system may be suitable for in vitro cytotoxicity testing: the total cellular-protein assay and the neutral red uptake assay which measure protein concentration in cells provide a quantifiable assay for the presence of living and dead cells.

The skin equivalent can be cultured in glass bottles or dishes, and the various chemicals to be tested applied to this cultured skin. By continuing to supply suitable culture media the skin will continue to grow until the test is complete.

The collagen sponge provides a temporary matrix which enables the rapid and sustained adherance of the composite living skin equivalent to a wound surface, in a human or animal, which provides a surface in contact with the wound surface that allows fibrovascular ingrowth from the wound surface and which allows for neodermal structures to develop. The collagen matrix is altered and gradually broken down and replaced by endogenous collagen as the fibroblasts interact with it physically and contribute to it biosynthetically. However, as the collagen sponges are cross-linked collagen, they do not contract and so can be stored for some time, and do not exhibit contraction when grafted onto wounds.

The pepsin-treated, non-porous collagen placed on the upper surface of the collagen sponge prevents invasion of the collagen sponge by cultured keratinocyte cells and thus ensures the compartmentalization of the skin equivalent into epidermal and dermal layers. This laminate layer is also gradually broken down to allow the normal interface between the dermis and epidermis to form.

The composite living skin equivalents of the present invention are approximately 0.8 mm thick and are therefore stronger than epidermal grafts and more easily handled during grafting. The success ("take") rate for the skin equivalents of the present invention is approximately 90%, which may be attributed to the presence of the dermal layer which promotes development of vascularization of the graft. Finally, the composite living skin equivalents of the present invention enables the graft to be applied in one stage, thereby requiring a only a single graft acceptance event. To facilitate transport and application of the composite living skin equivalent, vaseline gauze may be placed over the cultured graft.

The fibroblasts and keratinocytes used in accordance with the present invention may be either autogenic or allogenic. The use of allogenic cells enables the production and storage of the living skin equivalent of the present invention thereby avoiding delays in procuring grafts for the treatment of wounds. Both cell types, keratinocytes and fibroblasts could be stores frozen for months as single cell suspensions, using published methods. After thawing these cells were viable and grew readily in culture and thus were suitable to be sued for the production of skin equivalent. The skin equivalent has been grafted successfully to a human volunteer. Since cooling supresses the immunogenicity of skin grafts (Baldwin W M et al. Transplantation 1973; 15:419–422) cryopreservation of allogenic cells helps in attenuating some undesirable antigens. The availability of composite living skin equivalents for the treatment of surface area wounds can provide a virtually unlimited quantity of graftable skin as a source of permanent wound coverage.

The present invention will now be described in the following examples using human allogenic skin cells.

EXAMPLE 1

Composite grafts were made from separate, parallel cultures of allogenic human keratinocytes (HK) and human fibroblasts (HF) and a cellular bovine collagen membrane. The dermal membrane was modified using type 1 bovine collagen to provide a planar surface for cultured HKs.

Human skin was obtained from surgical specimens ie. neonatal circumcision (foreskin). After the excision the skin was placed in a sterile container with Dulbecco's modified Eagle's medium (DMEM). Specimens were delivered within a short time to the tissue culture laboratory where the epidermis was separated from the dermis enzymically according to the method of Eisinger,M (Method in Skin Research, Editor D. Skerrow 1985 p193).

Keratinocytes were cultured as a single cell suspension by the method of Eisinger which was modified as follows: HKs were cultured in DMEM supplemented with 2% fetal bovine serum, epidermal growth factor, insulin and hydrocortisone at pH 7.2. Confluent cultures were ready for harvest after 12 to 14 days either for subculture or for inoculation onto the collagen membrane.

Fibroblasts were released from dermal fragments by digesting these with *Clostridium histolyticum* collagenase. HFs were then grown in DMEM using standard methods.

The collagen sponge membranes (6 cm diameter), stored frozen in Petri dishes, were washed with sterile water and dehydrated in an incubator at 37° C. in order to compact the membranes. The sponges were then incubated overnight in DMEM supplemented with conditioned medium. Subconfluent cultures of HFs were innoculated at a density of $4\times10^5$ cells/ml onto the surface of the sponge. The sponge was then placed in DMEM in an incubator at 37° C., 5% carbon dioxide and saturated humidity for 10 days.

Medium was changed every second day. At the end of that period the sponges were turned over and a nonporous surface was prepared to provide a planar surface for cultured HKs.

Lamination was performed by applying a thin film of pepsin-treated, non-porous, sterile type 1 bovine collagen. The films were prepared from commercially available purified type 1 collagen which was pepsinized to remove teliopeptides and sterilized by Gamma radiation. The collagen solution was brought to neutral pH and applied as a thin film onto the surface of the collagen sponge and incubated for 60 minutes at 37° C.

Cultured HKs were then innoculated in drops at a density of $1\times10^5$ per drop on to the nonporous surface of the sponge and incubated for 10 days in DMEM with supplements mentioned above. Before clinical application culture medium without bovine pituitary extract was added to the culture dishes. Vaseline gauze was placed over the cultured graft to facilitate the transporting and securing of the graft to the wound bed.

In 8 operations performed on 5 children using the living skin equivalents of the present invention; the success rate was 90%.

Clinical and histological appearance of the above grafts in the eight operations of the RDEB children suggested that there was no rejection.

However, in order to determine direct evidence of the long term survival of cultured allografts or their contribution to permanent epithelium, clinical trials were performed on healthy adult volunteers described in the following example.

EXAMPLE 2

Composite grafts and allografts were derived the same way as outlined in Example 1. Having providing a planar surface for cultured keratinocytes, human keratinocytes where attached to the surface of the cross linked bovine collagen substrate. This "skin culture sandwich" was then transplanted on bloc on to the wound bed of human patients where the collagen matrix served as a framework to allow fibrovascular ingrowth from the underlying wound bed thus permitting human keratinocytes survival, and the formation of the neodermal structures.

Clinical studies were performed on four volunteers for the removal of decorative tatoos. Each volunteer had four skin areas excised on an arm. In two areas, the skin was excised down to the fat while the remaining two excisions left dermal elements in place. Full depth and partial thickness excissions were grafted with cultured skin and split thickness autograft skin (as controls). Weekly dressings were performed until the wounds were completely healed. The wounds were photographed, biopsies were performed for histology and DNA fingerprinting.

Figure 3:
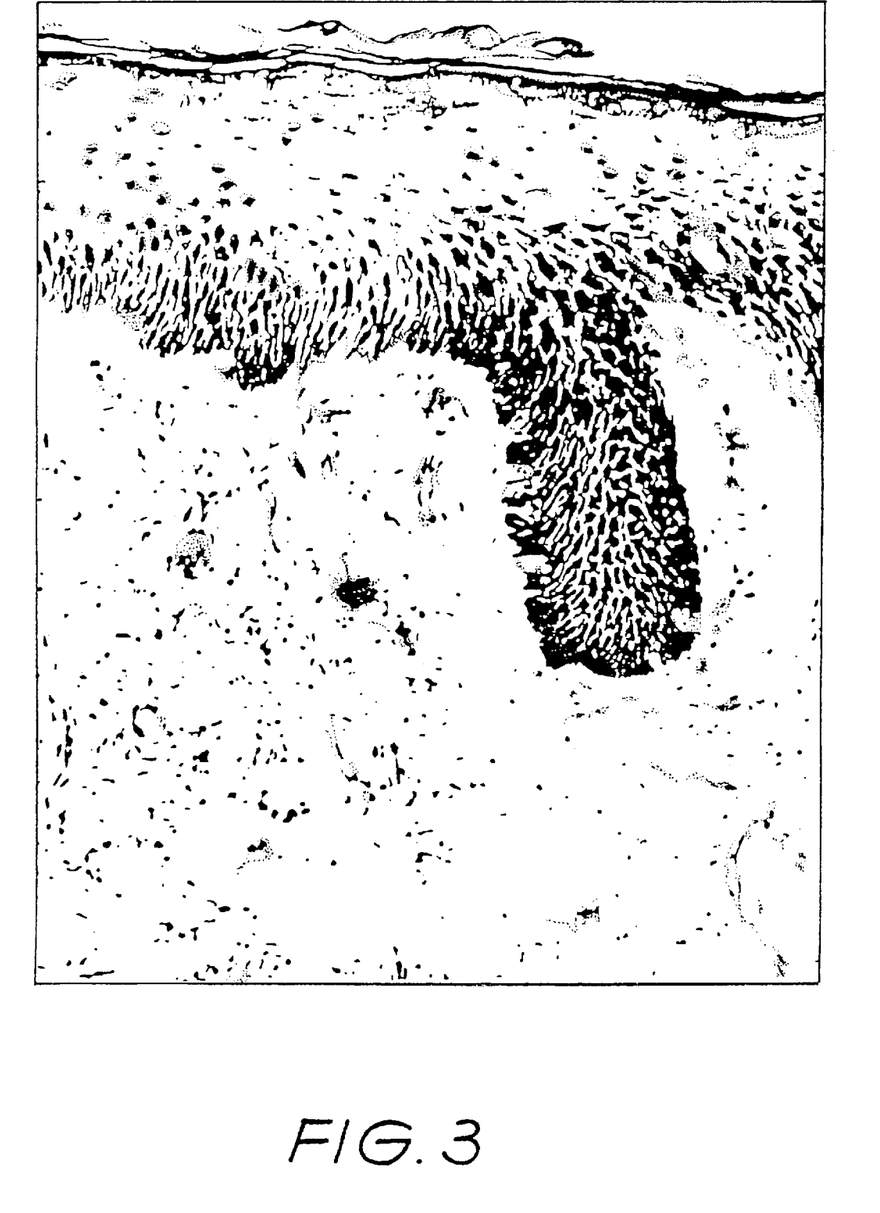
FIG. 3 shows the histology of a skin biopsy from a graft using the skin equivalent of the invention.
Figure 4:
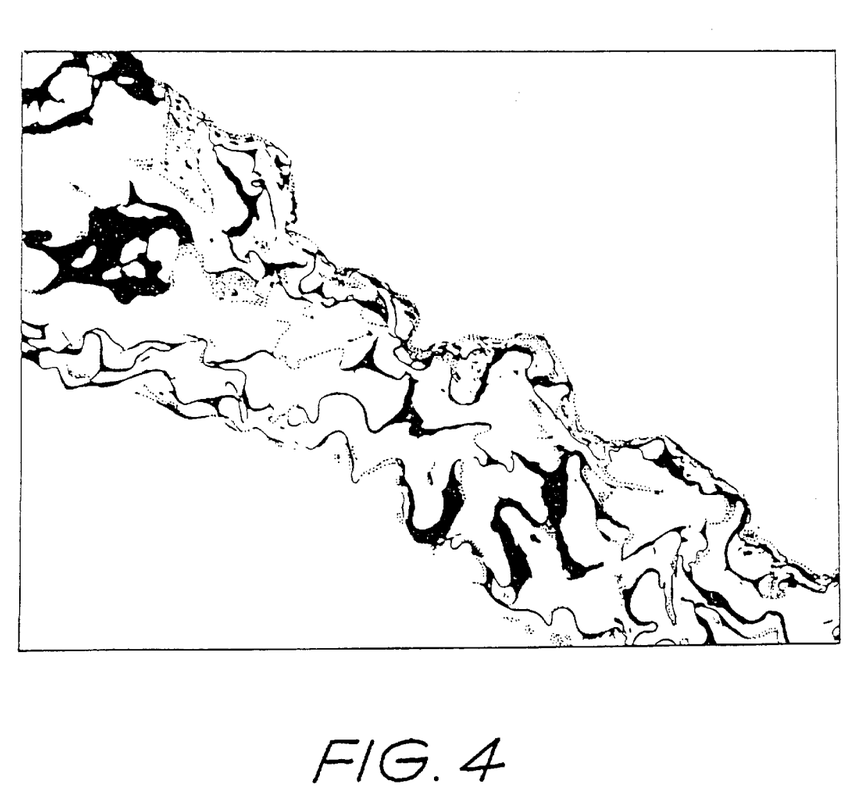
FIG. 4 shows the composite skin equivalent of the invention.
Figure 5:
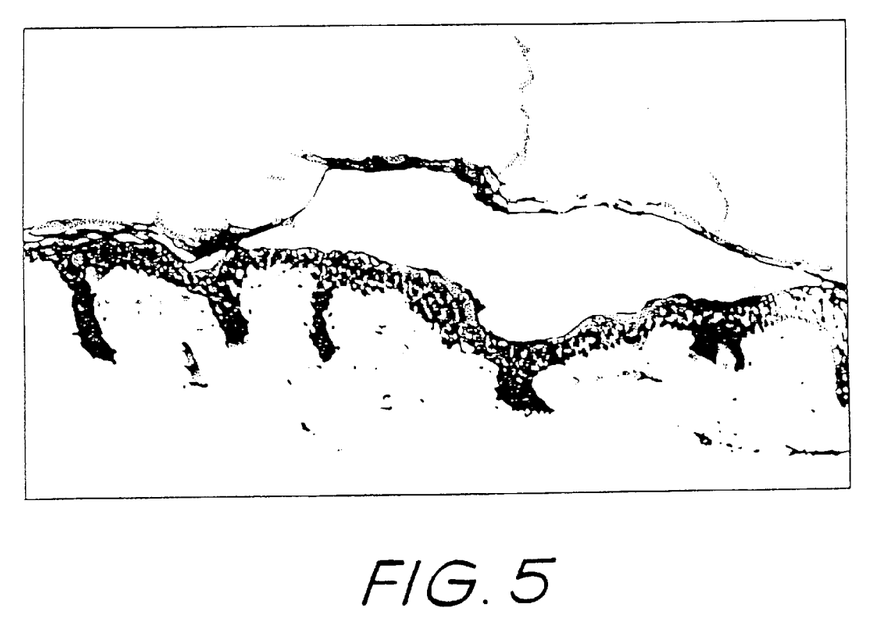
FIG. 5 shows a biopsy of the skin equivalent in a skin graft from a human subject.

Volunteer 1 had two areas grafted with cultured skin and the other two with an autograph. After 2 weeks the grafts had taken and there was no evidence of graft contraction. Biopsies of the central area of the grafts had a well differentiated and multilayered epidermis, and the dermis contained numerous fibroblasts and non-inflamatory cells in a loosely packed collagen matrix. FIGS. 3 and 5 show the histology of a skin biopsy from a cultured graft, 2 weeks postoperatively. FIG. 4 shows the skin equivalent before grafting. DNA fingerprinting indicated that there was a mixed population of cells both donor and recipient indicating that some of the dermal cells were derived from the patients since there was evidence of marked dermal cellularity.

Volunteer 2. The graft did not take in any of the areas. At three weeks there was histological evidence of a granulating wound.

Volunteer 3. After 4 weeks all the grafts had healed without any contraction. From a histology examination, there was a fully differentiated epidermis and a hypecellular dermis. DNA fingerprinting showed a mixed population of donor and recipient cells.

Volunteer 4. After 8 weeks the graft showed some contraction (approximately 15–20%) with the central graft area of this patient had a fully differentiated epidermis and a mature dermis without adnexae.

It should be obvious to persons skilled in the art that numerous variations and modifications could be made to the invention as described above, without departing from the overall scope and spirit of the present invention.

I claim:

1. A composite which comprises relative to a horizontal plane:
   a) a first layer comprising a collagen matrix having upper and lower surfaces, said matrix being capable of permitting the growth of fibroblast cells therein, and being essentially non-contractible,
   b) a non-porous second layer essentially free of exogenous glycosaminoglycans, said layer comprising a non-porous collagen layer having upper and lower surfaces, the lower surface thereof being in contact with the upper surface of said first layer, and being sufficiently non-porous to be capable of maintaining on its surface keratinocyte cells without the substantial invasion of said cells into said collagen matrix.

2. The composite of claim 1 wherein a layer comprising cultured keratinocyte cells is in contact with the upper surface of said non-porous collagen second layer.

3. The composite of claim 1 wherein said collagen matrix contains cultured fibroblast cells therein.

4. The composite of claim 2 wherein said collagen matrix contains cultured fibroblast cells therein.

5. The composite of claim 1 wherein the collagen matrix is crosslinked collagen.

6. The composite of claim 5 wherein the collagen of at least one of the layers is bovine source derived.

7. The composite of claim 6, wherein the non-porous collagen is selected from the group consisting of Type 1 collagen, Type 3 collagen, and mixtures thereof.

8. The composite of claim 7, wherein the non-porous collagen has been pre-treated with pepsin.

9. The composite of claim 2 wherein the collagen matrix is crosslinked collagen.

10. The composite of claim 9 wherein the collagen of at least one of the layers is bovine source derived.

11. The composite of claim 10, wherein the non-porous collagen is selected from the group consisting of Type 1 collagen, Type 3 collagen, and mixtures thereof.

12. The composite of claim 11, wherein the non-porous collagen has been pre-treated with pepsin.

13. The composite of claim 12 wherein the non-porous collagen second layer is applied to said upper surface of said first layer as a thin film from a solution of collagen.

* * * * *